(12) United States Patent
Restelli et al.

(10) Patent No.: US 6,419,658 B1
(45) Date of Patent: Jul. 16, 2002

(54) DISPOSABLE SAFETY SYRINGE

(76) Inventors: Sergio Restelli, Via Quarto Peperino 333 B, 00100 Roma; Nardino Righi, Viale Lombardia 117, 20100 Cologno Monzese (Milano); Roberto Rossi, Via Delle Ande 10, 20151 Milano, all of (IT)

( * ) Notice: Subject to any disclaimer, the term of this patent is extended or adjusted under 35 U.S.C. 154(b) by 0 days.

(21) Appl. No.: 09/600,643
(22) PCT Filed: Jan. 18, 1999
(86) PCT No.: PCT/EP99/00222
§ 371 (c)(1),
(2), (4) Date: Jul. 20, 2000
(87) PCT Pub. No.: WO99/37345
PCT Pub. Date: Jul. 29, 1999

(30) Foreign Application Priority Data

Jan. 20, 1998 (IT) .......................................... SV98A0003

(51) Int. Cl.⁷ .................................................. A61M 5/00
(52) U.S. Cl. ...................................... 604/110; 604/198
(58) Field of Search ................................. 604/110, 187, 604/192, 195, 197, 198, 263

(56) References Cited

U.S. PATENT DOCUMENTS

| | | | |
|---|---|---|---|
| 4,998,924 A | * 3/1991 | Ranford | 604/798 |
| 5,045,066 A | * 9/1991 | Scheuble et al. | 604/198 |
| 5,141,500 A | * 8/1992 | Hake | 604/198 |
| 5,163,918 A | * 11/1992 | Righi et al. | 604/198 |
| 5,269,761 A | * 12/1993 | Stehrenberger et al. | 604/110 |
| 5,290,255 A | * 3/1994 | Vallelunga et al. | 604/197 |
| 5,314,414 A | * 5/1994 | Hake et al. | 604/198 |
| 5,562,624 A | * 10/1996 | Righi et al. | 604/110 |
| 5,611,782 A | * 3/1997 | Haedt | 604/198 |
| 6,319,234 B1 | * 11/2001 | Restelli et al. | 604/198 |

* cited by examiner

Primary Examiner—Gregory Huson
Assistant Examiner—Huyen Le
(74) Attorney, Agent, or Firm—Sughrue Mion, PLLC

(57) ABSTRACT

A needle-covering sleeve (14), slidably fitted on the syringe barrel (1), is held in its retracted rest position by means of retaining tongues (10), which hook it at its rear rim (13). At the end of the injection stroke of the plunger (2), a rear flange (8) of the stem (3) of the plunger (2) radially opens the retaining tongues (10) apart, which release thereby the needle-covering sleeve (14). Then, the latter is axially advanced by means of a spring (16), to an advanced safety position, in which it entirely covers the needle (5) and is fastened to a sleeve-clamping ring (18), which is provided at the fore end of the syringe barrel (1). To this purpose, the sleeve-clamping ring (18) has peripheral elastic retaining tongues (19) which interact with matching retaining teeth (20) on the inner part of needle-covering sleeve (14) and prevent any axial backward movement of the needle-covering sleeve (14). Further, the sleeve-clamping ring (18) is a stop abutment, cooperating with an inner projection of the needle-covering sleeve (14) and preventing any further axial forward movement of such sleeve.

17 Claims, 4 Drawing Sheets

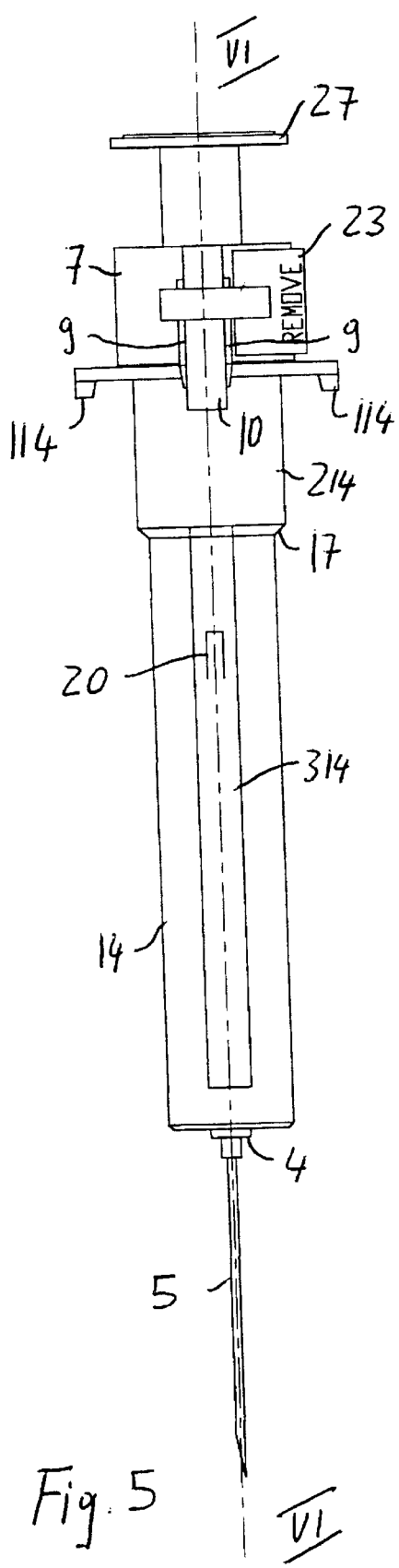
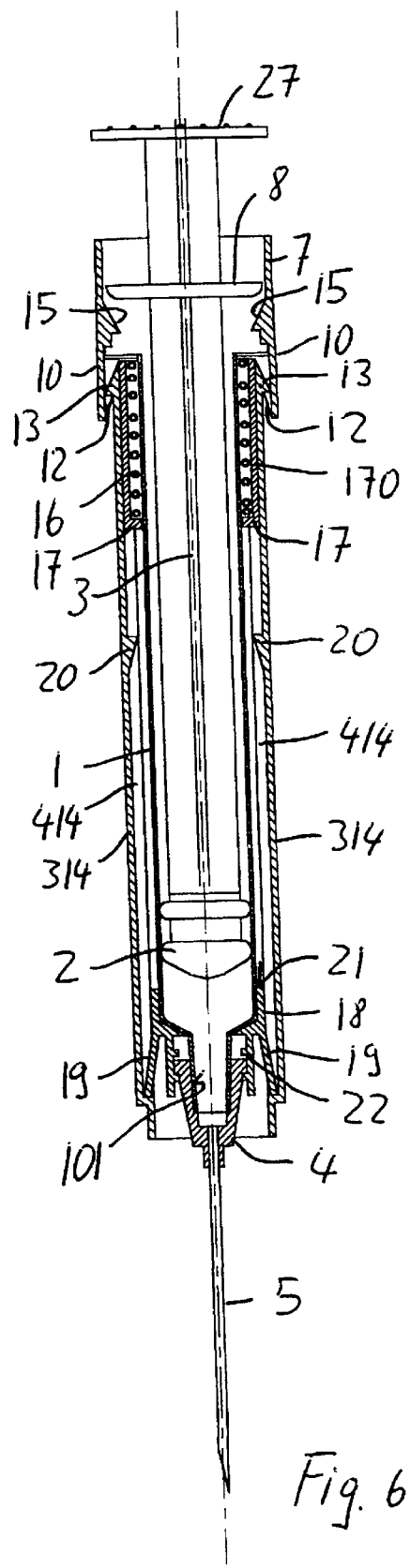
Fig. 5
Fig. 6

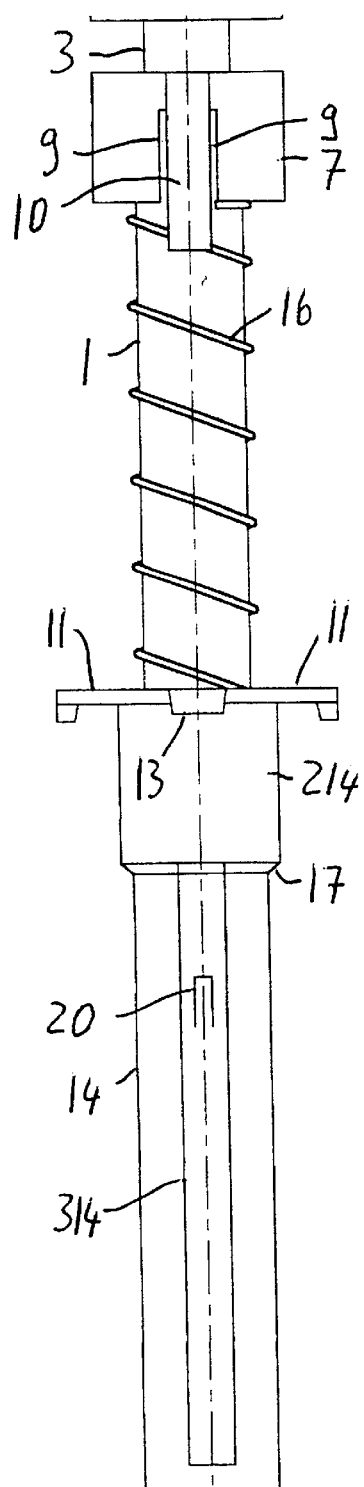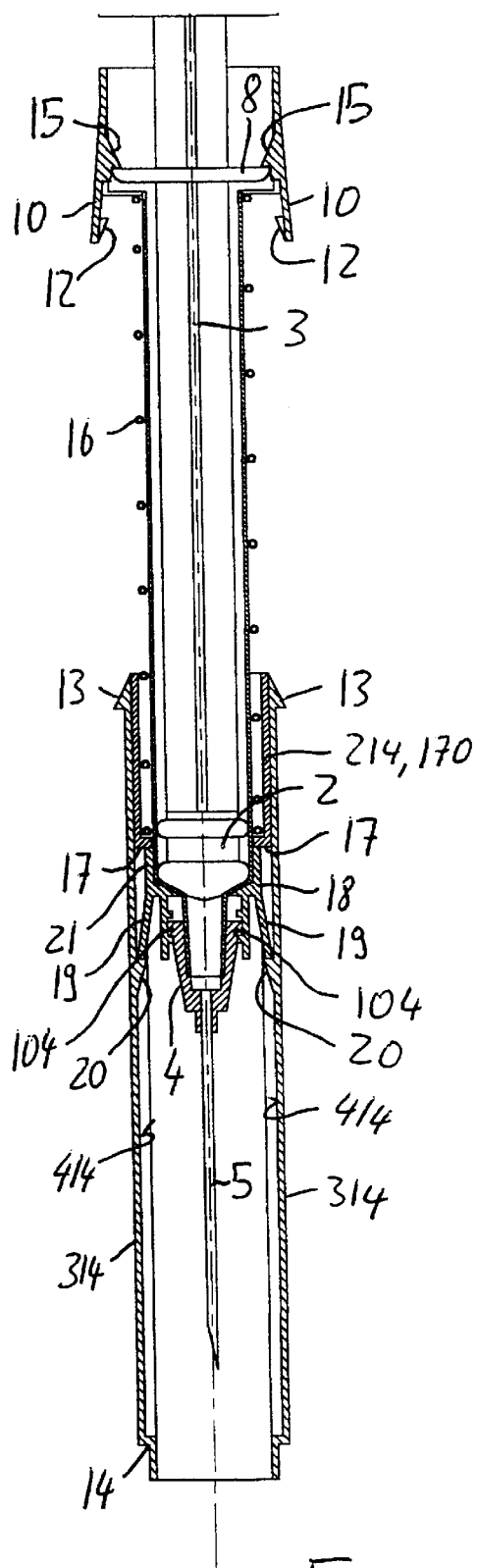
Fig. 7
Fig. 8

DISPOSABLE SAFETY SYRINGE

SUMMARY OF THE INVENTION

The present invention relates to a disposable safety syringe comprising:

a) a syringe barrel;

b) an injection needle, being integral with a needle-carrier, which is fitted on the tapered fore end of the syringe barrel;

c) a plunger which is slidable in the syringe barrel and has an injection stroke which extends from a retracted syringe-filling position to an advanced syringe-emptying position, and is fitted at its back with a manually drivable stem, driven out of the syringe barrel through the open rear end thereof;

d) a needle-covering sleeve, which is axially fitted on the syringe barrel, so as to slide from a retracted rest position, in which it leaves the needle exposed, into an advanced safety position, in which it entirely covers the needle;

e) hook-like interacting means, which are provided at the rear side of the syringe barrel and at the rear side of the needle-covering sleeve, and are initially engaged with each other so as to retain the needle-covering sleeve in its retracted rest position, whereas they are automatically disengaged from each other by the plunger stem, in the last portion of the injection stroke of the plunger, thereby releasing the needle-covering sleeve;

f) a spring, interposed between a spring-bearing projection on the rear end of the syringe barrel and a spring-bearing projection, inside the needle-covering sleeve, which stresses the needle-covering sleeve, once it is released from the hook-like means, towards its advanced safety position, first by making it elastically adhere to the patient body, and then by progressively advancing it, on extracting the needle from the patient body, at the end of the injection, until it entirely covers the extracted needle;

g) clamping means which automatically lock the needle-covering sleeve in its advanced safety position, preventing it from axially moving in either direction;

h) the means for locking the needle-covering sleeve in its advanced safety position are held and/or formed at least partially by a mounted sleeve-clamping ring, which is provided and preferably mounted and fitted on the fore end of the syringe barrel.

i) one or more retaining tongues, preferably formed of one piece with the sleeve-clamping ring and extending forwards in the axial direction by their free fore ends, which retaining tongues may be elastically moved radially inwards, that is towards the longitudinal axis of the syringe;

k) one or more retaining teeth provided on the inner part of the needle-covering sleeve, each associated to a tongue for retaining the sleeve-clamping ring, each of these retaining teeth being provided with a rear flank which is substantially transverse to the longitudinal axis of the syringe and interacts as a bearing surface with the free end of the retaining tongue associated thereto, and with a fore flank, which is inclined forwardly radially outwards and interacts as a deflecting surface with the free end of the retaining tongue associated thereto;

l) a radial stop projection, which is provided at the rear end of the sleeve-clamping ring and interacts as an abutment with an inner stop projection of the needle-covering sleeve;

m) all this in such a way that, in the last portion of the forward stroke of the needle-covering sleeve, the retaining tooth/teeth thereof elastically and radially push, by their inclined fore flanks, the associated retaining tongue/s inwards, passing beyond them, and enabling them to elastically snap radially outwards, so as to engage their free fore ends with the transverse rear flanks of the associated retaining tooth/teeth, while the inner stop projection of the needle-covering sleeve contacts the rear abutment projection of the sleeve-clamping ring.

DESCRIPTION OF THE PRIOR ART

A disposable safety syringe of this kind is known from the documents U.S. Pat. No. 5,562,626, WO-A-93/00949 and EP-A-0 467 173. In the disposable safety syringes known from these documents, the needle-covering sleeve has an all around circular inner section profile and an all around circular smooth outer section profile, and the retaining teeth which cooperate with the retaining tongues of the sleeve-clamping ring protrude inwardly from said circular inner section profile of the needle-covering sleeve, thus determining a corresponding outer diameter of said sleeve.

With respect to these known syringes, the disposable safety syringe according to the invention is characterized in that the retaining tongues of the sleeve-clamping ring are slidably engaged by their free fore ends in corresponding inner longitudinal grooves of the needle-covering sleeve, in which grooves their respective retaining teeth are provided, and said inner longitudinal grooves of the needle-covering sleeve are formed in corresponding outer longitudinal ribs of the needle-covering sleeve.

DETAILED DESCRIPTION OF THE DRAWINGS

Such characteristics, and further more, of the invention, as well as the advantages deriving therefrom will be apparent from the following description of a preferred embodiment, illustrated without restriction in the accompanying drawings, in which:

FIG. 5 is a side view of the syringe of FIG. 1, with the needle-covering sleeve in its retracted rest position.

FIG. 6 is an axially sectional view of the syringe as taken on line VI—VI of FIG. 5, also in the retracted rest position of the needle-covering sleeve.

FIG. 7 is a side view of the syringe, like that of FIG. 5, but with the needle-covering sleeve in its advanced safety position, when the injection has been made and when the needle has been extracted from the patient body.

FIG. 8 is an axially sectional view of the syringe, as taken on line VIII—VIII of FIG. 7, also in the advanced safety position of the needle-covering sleeve.

DETAILED DESCRIPTION OF THE PRESENT INVENTION

Figure 1:
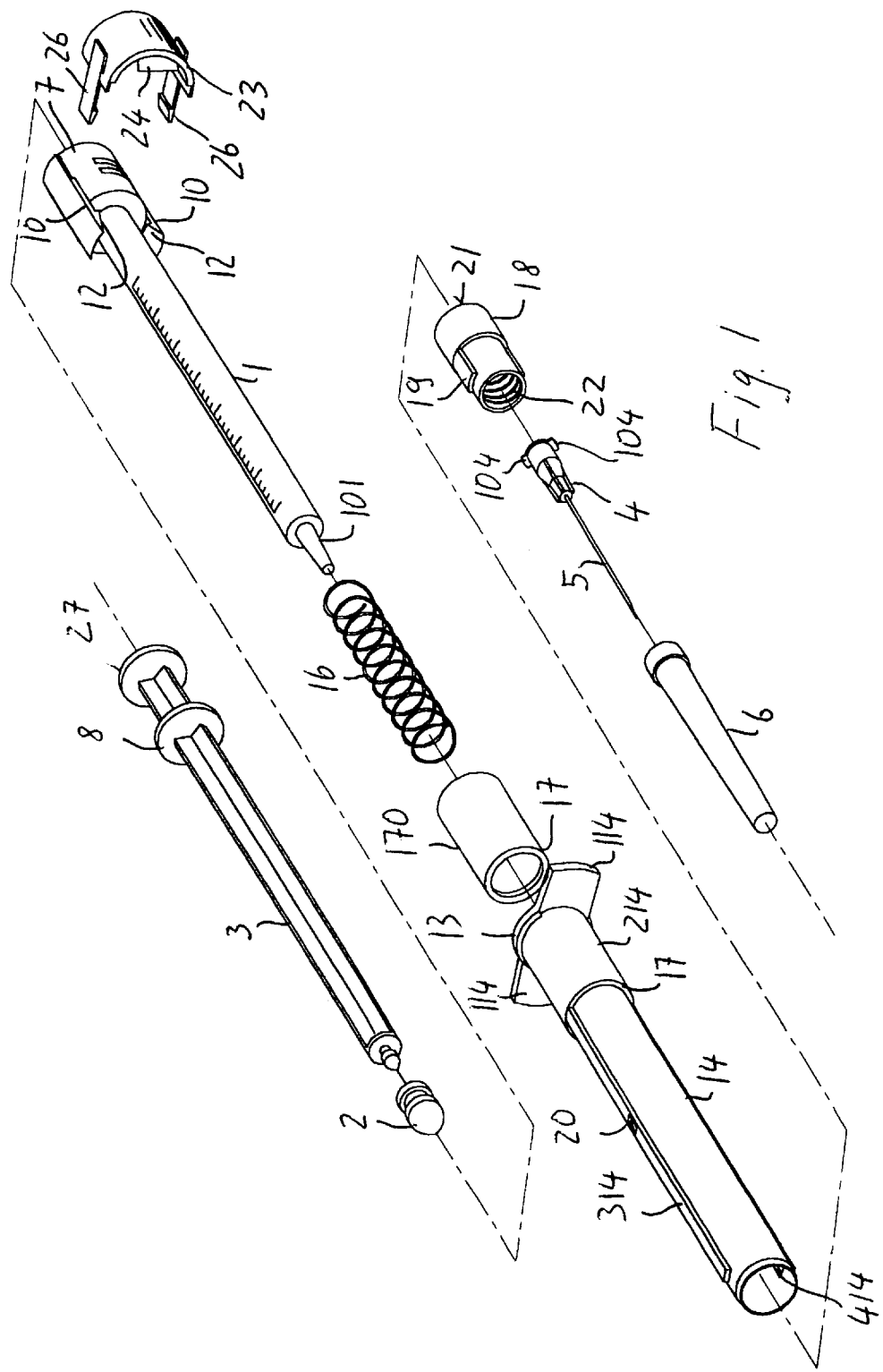
FIG. 1 is an exploded, perspective view of an embodiment of the syringe according to the invention.

The disposable safety syringe according to the invention comprises a cylindrical barrel 1, in which a plunger 2 is slidable in a fluid-tight manner. The plunger 2 is attached to a stem 3, which extends axially in the syringe barrel 1 and is driven out of it, through its open rear end. On the conical tapered fore end 101 of the syringe barrel 1, a needle-carrying member 4 is attached in a fluid-tight manner, the injection needle 5 being fixed thereto. The inner space of the syringe barrel 1 communicates with the tubular injection needle 5, through a hole formed in the needle-carrier 4. The needle 5 is initially protected by a cap 6, fitted on the needle-carrier 4. The needle-carrier 4 and the needle 5 are omitted in the sectional view of FIG. 6.

The syringe barrel 1 is provided, at its rear end, with a hollow widened head 7, open at its back, wherein a flange 8, for example having a circular shape, and provided on the stem 3 of the plunger 2 near the rear end of such stem 3 is housed. On two diametrically opposite locations, on the side wall of the head 7 of the syringe barrel, two retaining tongues 10 are formed by means of cuts 9, forwardly extending in the longitudinal direction beyond the fore edge of the head 7. The retaining tongues 10 are provided, at their fore free ends, with a hook-like radially inward tooth 12 which interacts with an associated hook-like radially outward counter-tooth 13, placed on the upper edge of a needle-covering sleeve 14, which is provided with two radial diametrically opposite flanges 114 and is axially slidably fitted on the syringe barrel 1. Normally, in the rest condition, the retaining tongues 10 are in a radially retracted position, i.e. substantially parallel to the longitudinal axis of the syringe and in which their hook-like teeth 12 are engaged with their respective hook-like counter-teeth 13 of the needle-covering sleeve 14, as shown in FIG. 6. However, said retaining tongues 10 may be elastically opened apart and brought to a position in which their hook-like teeth 12 are disengaged from their associated hook-like counter-teeth 13 of the needle-covering sleeve 14, as shown in FIG. 8.

In order to obtain such radially opened apart position of the retaining tongues, each retaining tongue 10 is provided—on its radially inner side—with a projection 15, protruding inside the hollow head 7 of the syringe barrel 1 and having a saw-tooth profile, with a surface which, when seen from back to front, is inclined inwards, i.e towards the central axis of the syringe, and terminates by an undercut step. These inner projections 15 of the retaining tongues 10 interact with the flange 8 of the stem 3 of the plunger 2 as described below.

For a certain portion 214 of its rear end part, the needle-covering sleeve 14 has an inside diameter which is greater than the outside diameter of the syringe barrel 1, and the hollow space therebetween houses a helical spring 16 resting by its upper end, as seen from the outside, against the annular bottom of the widened head 7 of the syringe barrel 1, and by its fore end against a spring-bearing projection 17 which is provided inside the needle-covering sleeve 14 and may consist of the annular bottom of the rear widened part 214 of the needle-covering sleeve 14 or, as shown, of a bushing 170 inserted in said widening and having, on one end side, an annular rim which projects radially inwards, and arranged to form such spring-bearing projection 17. The remaining portion of the needle-covering sleeve 14 is provided with two outer diametrically opposite longitudinal ribs 314, extending from the annular bottom of the rear widened part 214 of the needle-covering sleeve 14, to a little before its fore end. The outer surface of said outer longitudinal ribs 314 is preferably substantially in line with the outer surface of the rear widened part 214 of the needle-covering sleeve 14. Each outer longitudinal rib 314 of the needle-covering sleeve 14 forms a corresponding inside longitudinal groove 414.

A sleeve-clamping ring 18 is fitted and mounted on the fore cylindrical end of the syringe barrel 1, and extends forwards around the conical tapered end 101 of the syringe barrel and around the needle-carrier 4 fitted on said conical tapered end 101. This sleeve-clamping ring 18 preferably has, at its periphery, two retaining tongues 19, which are made of one piece with said ring 18 and extend in the axial direction, with their free ends being directed forwards. Said retaining tongues 19 are situated on two radially opposite locations and are radially opened apart i.e. inclined forwardly and radially outwards, while being elastically movable radially inwards. The free fore ends of said retaining tongues 19 are each engaged in one of the inner longitudinal grooves 414 of the needle-covering sleeve 14, formed in the corresponding outer longitudinal ribs 314. In each of these inner longitudinal grooves 414 of the needle-covering sleeve 14, there is provided a retaining tooth 20, which is arranged to interact with the free fore end of the associated retaining tongue 19 of the sleeve-clamping ring 18 as described below. Each of these retaining teeth 20 has a rear flank, which is substantially plane and transverse to the syringe axis, and a fore flank which is inclined forwardly radially outwards.

The rear end of the sleeve-clamping ring 18 radially projects from the peripheral surface of the syringe barrel 1 and forms an annular abutment 21, arranged to interact with the inner spring-bearing projection 17 of the needle-covering sleeve 14 as described below.

The sleeve-clamping ring 8 may be stably and unremovably fastened to the syringe barrel 1, for example by gluing or welding, or may be force-fitted on the fore end of the syringe barrel 1 and thus removably held thereon by friction. The sleeve-clamping ring 18 may be also completely separated and disengaged from the needle-carrier 4. However, in the illustrated embodiment, the sleeve-clamping ring 18 is mechanically bound to the needle-carrier 4 and hence to the needle-carrier 5, at least in the axial direction. Particularly, the sleeve-clamping ring 18 has an inner thread 22, wherein the needle-carrier 4 is screwed with the help of outer radial wings 104 of its rear rim.

The above disposable safety syringe operates as follows.

Figure 2:
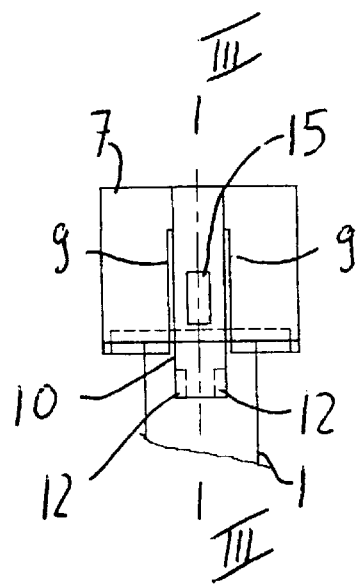
FIG. 2 is a side view of the rear end of the syringe barrel.
Figure 3:
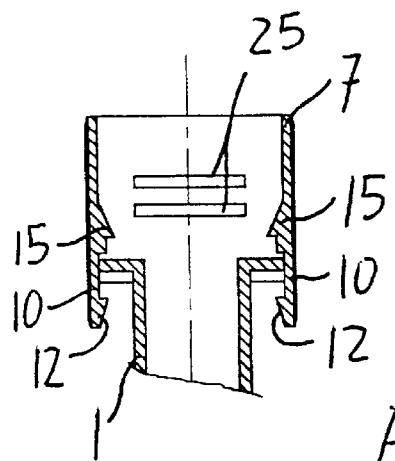
FIG. 3 is an axially sectional view of the rear end of the syringe barrel, as taken on line III—III of FIG. 2.
Figure 4:
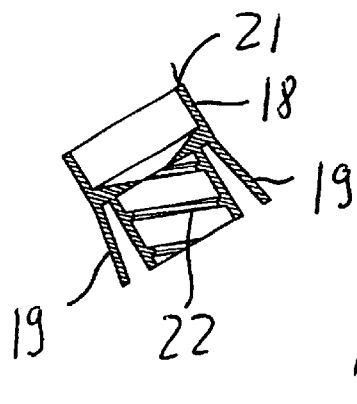
FIG. 4 is an axially sectional view of the sleeve-clamping ring provided at the fore end of the syringe barrel.

In the initial condition, i.e. the user-supplied condition, the different parts of the syringe are in the positions shown in FIGS. 2 and 3. More precisely, the needle-covering sleeve 14 is in a retracted rest position, in which it leaves the needle 5 exposed, and is held and hooked by the retaining tongues 10, which are free and thus in their radially inwardly inclined position. The retaining tongues 19 of the sleeve-clamping ring 18 are opened apart and engaged in the fore end part of their respective inner grooves 414 of the needle-covering sleeve 14. The helical spring 16 is compressed and entirely housed in the rear widened part 214 of the needle-covering sleeve 14, between the latter and the syringe barrel 1. The retaining tongues 10 are preferably as long as to hook and retain the needle-covering sleeve 14 in a retracted position, in which its rear rim is close to the head 7 of the syringe barrel 1, whereby the spring is actually invisible, and the side wings 114 of the needle-covering sleeve 14 are disposed immediately before the head 7 of the syringe barrel 1. The plunger 2 and its stem 3 lie in an advanced position, in which the plunger 2 is close to the fore end of the syringe barrel 1, but is still able to run a small forward stroke. The rear flange 8 of the stem 3 of the plunger 2 is partially inserted in the rear hollow head 7 of the syringe barrel 1, but is stopped in a position, in which it does not come into contact with the inner slanted projections 15 of the retaining tongues 10, or only touches said projections 15, without exerting any perceptible pressure thereon.

In the illustrated embodiment, the flange 8 is stopped by means of a safety cylindrical sector 23, which extends outside the hollow cylindrical head 7 of the syringe barrel 1, covering an angle substantially equal to or less than 180°, and has two inner clamping tongues 24 which extend transverse and perpendicular to the syringe axis, while being parallel to and at a distance from each other. These clamping tongues 24 are inserted inside the head 7 of the syringe barrel 1 through two corresponding slots 25, formed in the lateral cylindrical shell of said head 7 and are disposed one behind the other before the rear flange 8 of the stem 3 of the plunger 2, thereby locking said flange 8 in the above mentioned position, in which it does not interfere with the inner projections 15 of the retaining tongues 10. In the above mentioned locking position, the safety cylindrical sector 23 is removably bound to the head 7 of the syringe barrel 1, for example by means of two hook-like side levers 28, made of one piece with the cylindrical sector 23, so that they can oscillate elastically about an intermediate point of their length. Initially, said side levers 26 are hooked by a toothed end thereof to corresponding outer projections of the head 7 of the syringe barrel 1. By exerting pressure radially on the other end of said side levers 26, the latter are angularly displaced and released from the associated outer projections of the head 7 of the syringe barrel 1, whereby the safety cylindrical sector 23 is disengaged from said head 7. Then, this safety sector 23 may be removed, radially, by pulling its inner clamping tongues 24 out of their respective side slots 25 of the head 7 of the syringe barrel 1, and thereby releasing the flange 8 of the stem 3 of the plunger 2, and thus the stem 3 itself. Instructions for use may be provided outside the safety sector of a cylinder 23.

Once the safety cylindrical sector 23 is torn off and the protective cap 6 of the needle 5 is removed, the latter may be introduced, for example, in an ampoule containing the to-be-injected liquid, and this liquid may be aspirated in the syringe, by pulling the plunger 2 back to a syringe-filling position, by means of an end head 27, provided at the rear end of the stem 3, outside the hollow head 7 of the syringe barrel 1.

The syringe being so filled, the injection is made in the usual way, since the needle-covering sleeve 14 is still hooked and held by the retaining tongues 10 in its retracted rest position, as shown in FIG. 6, in which it leaves the needle 5 exposed. The side wings 114 provided at the rear end of the needle-covering sleeve 14 are used to hold the syringe barrel 1 during the injection, for example by grasping them in the usual way, by the index and middle fingers of a hand, while axial pressure is exerted on the rear end head 27 of the stem 3 of the plunger 2, for example by the thumb of the same hand.

In the final part of the injection stroke of the plunger 2, the flange 8 of the stem 3 penetrates in the hollow head 7 of the syringe barrel 1 more deeply than before, for example up to the bottom of said head, or anyway to such an extent as to engage and push the inner projections 15 of the retaining tongues 10 radially outwards, and as to radially open, i.e. as to outwardly angularly deflect said retaining tongues 10, as shown in FIG. 8. While being opened apart, the retaining tongues 10 disengage and release the needle-covering sleeve 14, which is pushed by the spring 16 and advanced on the syringe barrel 1 until it adheres by its fore end against the part of the patient body, in which the needle 5 is inserted. Then, while the needle 5 is extracted from the patient body, the needle-covering sleeve is further advanced with respect to the syringe barrel 1 by the spring 16, until it reaches a final advanced safety position, in which besides entirely covering the needle 5, it also extends beyond the pointed end thereof, to such an extent as to prevent the needle to be accessed by a finger, as shown in FIGS. 7 and 8.

In the advanced safety position, the needle-covering sleeve 14 is axially clamped in both directions by the sleeve-clamping ring 18. More precisely, in the last part of the forward stroke run by the needle-covering sleeve 14, the inner retaining teeth 20 of said sleeve elastically and radially push, by their inclined fore flank, acting as a deflecting surface, the associated retaining tongues 19 of the sleeve-clamping ring 18, whereupon the retaining teeth 20 pass beyond their respective retaining tongues 19, which elastically snap outwards, going back to their rest position, in which their free fore ends are engaged with the rear transverse flanks of the associated retaining teeth 20 of the needle-covering sleeve 14. At the same time, the spring-bearing projection 17 inside the needle-covering sleeve 14 reaches or nearly reaches the rear end 21 of the sleeve-clamping ring 18, acting as a stop abutment, as shown in FIG. 8. By this arrangement, the chuck-clamping ring 18 fits between the inner retaining teeth 20 of the needle-covering sleeve 14 and the spring-bearing projection 17 inside it, thereby axially locking the needle-covering sleeve 14 to the syringe barrel 1 in both directions in its advanced safety position. When the chuck-clamping ring 18 is stably unremovably fastened to the syringe barrel 1, the needle-covering sleeve 14 is also stably and unremovably fastened to the syringe barrel 1 and the syringe has to be intentionally broken to access the needle 5. When the chuck-clamping ring 18 is removably fitted on the syringe barrel 1 and is held thereon by friction, any attempt to forcibly pull forwards the needle-covering sleeve 14 causes the chuck-clamping ring 18 to be axially detached, so that it is removed together with the needle-covering sleeve 14 and with the needle 5, the needle-carrier 4 being screwed in the chuck-clamping ring 18. So the needle 5 is inaccessibly confined inside the needle-covering sleeve 14 slipped out of the syringe barrel 1.

Once the injection has been made, the stem 3 of the plunger 2 is automatically locked in both axial directions to the syringe barrel 1 in the advanced position of the plunger 2, i.e. in its syringe-emptying position, thereby preventing any further movement of the plunger 2 and any reuse of the syringe. To this end, when the retaining tongues 10 of the rear head 7 of the syringe barrel 1 have been opened apart, and when the needle-covering sleeve 14 has been released thereby by interacting with the inclined deflecting surfaces of the inner projections of the retaining tongues 10, the rear flange 8 of the stem 3 of the plunger 2 passes beyond said projections 15, enabling the retaining tongues 10 to elastically snap radially inwards and to go back to their initial rest position, in which the flange 8 of the stem 3 of the plunger 2 now fits and is clamped between the annular bottom of the rear head 7 of the syringe barrel 1 and the undercut step of the projections 15 of the retaining tongues 10, as shown in FIG. 8. Consequently, the stem 3 and the plunger 2 are also locked.

According to a variant embodiment (not shown), in order to automatically prevent the stem 3 of the plunger 2 from moving axially backwards from the syringe-emptying position, instead of using the projections 15 of the retaining tongues 10, there are provided one or more appropriate reverse-lock clamping teeth on the inner wall of the rear hollow head 7 of the syringe barrel 1, the elastic deformation of said reverse-lock clamping teeth and/or of said flange 8 being exploited to enable said flange 8 to pass beyond said teeth.

All the parts of the syringe according to the invention, except the needle 5, are generally made of plastic.

Naturally, the invention is not limited to the embodiments described and illustrated herein, but may be greatly varied, especially as regards construction and within the range of equivalents, without departure from the guiding principle disclosed above and claimed below.

What is claimed is:

1. A disposable safety syringe, comprising:

a) a syringe barrel (1);

b) an injection needle (5), being integral with a needle-carrier (4), which is fitted on the tapered fore end (101) of the syringe barrel (1);

c) a plunger (2) which is slidable in the syringe barrel (1) having an injection stroke which extends from a retracted syringe-filling position to an advanced syringe-emptying position, and is fitted at its back with a manually drivable stem (3), driven out of the syringe barrel (1) through the open rear end thereof;

d) a needle-covering sleeve (14), which is axially fitted on the syringe barrel (1), so as to slide from a retracted rest position, in which it leaves the needle (5) exposed, into an advanced safety position, in which it entirely covers the needle (5);

e) hook-like interacting means (12, 13), which are provided at the rear side of the syringe barrel (1) and at the rear side of the needle-covering sleeve (14), and are initially engaged with each other so as to retain the needle-covering sleeve (14) in its retracted rest position, whereas they are automatically disengaged from each other by the stem (3) of the plunger (2), in the last portion of the injection stroke of the plunger (2), thereby releasing the needle-covering sleeve (14);

f) a spring (16), interposed between a spring-bearing projection on the rear end of the syringe barrel (1) and a spring-bearing projection (17), inside the needle-covering sleeve (14), which stresses the needle-covering sleeve (14), once it is released from the hook-like means (12, 13), towards its advanced safety position, first by making it elastically adhere to the patient body, and then by progressively advancing it, on extracting the needle (5) from the patient body, at the end of the injection, until it entirely covers the extracted needle (5);

g) clamping means (19, 21) which automatically lock the needle-covering sleeve (14) in its advanced safety position, preventing it from axially moving in either direction;

h) the means (19, 21) for locking the needle-covering sleeve (14) in its advanced safety position are held and/or formed at least partially by a mounted sleeve-clamping ring (18), which is provided and preferably mounted and fitted on the fore end of the syringe barrel (1);

i) one or more retaining tongues (19), formed of one piece with the sleeve-clamping ring (18) and extending forwards in the axial direction by their free fore ends, which retaining tongues may be elastically moved radially inwards, that is towards the longitudinal axis of the syringe;

k) one or more retaining teeth (20) provided on the inner part of the needle-covering sleeve (14), each associated to a tongue (19) for retaining the sleeve-clamping ring (18), each of these retaining teeth (20) being provided with a rear flank which is substantially transverse to the longitudinal axis of the syringe and interacts as a bearing surface with the free end of the retaining tongue (19) associated thereto, and with a fore flank, which is inclined forwardly radially outwards and interacts as a deflecting surface with the free end of the retaining tongue (19) associated thereto;

l) a radial stop projection (21), which is provided at the rear end of the sleeve-clamping ring (18) and interacts as an abutment with an inner stop projection (17) of the needle-covering sleeve (14);

m) all this in such a way that, in the last portion of the forward stroke of the needle-covering sleeve (14), the retaining tooth/teeth (20) thereof elastically and radially push, by their inclined fore flanks, the associated retaining tongue/s (19) inwards, passing beyond them, and enabling them to elastically snap radially outwards, so as to engage their free fore ends with the transverse rear flanks of the associated retaining tooth/teeth (20), while the inner stop projection (17) of the needle-covering sleeve (14) contacts the rear abutment projection (21) of the sleeve-clamping ring (18), characterized in that the retaining tongues (19) of the sleeve-clamping ring (18) are slidably engaged by their free fore ends in corresponding inner longitudinal grooves (414) of the needle-covering sleeve (14), in which grooves (414) their respective retaining teeth (20) are provided, and said inner longitudinal grooves (414) of the needle-covering sleeve (14) are formed in corresponding outer longitudinal ribs (314) of the needle-covering sleeve (14).

2. A syringe as claimed in claim 1, characterized in that the needle-covering sleeve (14) is provided, at its rear edge, with one or more outwardly projecting hook-like teeth (13), interacting with one or more complementary inwardly projecting hook-like teeth (12), provided on retaining tongues (10) which extend forward in the longitudinal direction of the syringe, from a head (7), located at the rear end of the syringe barrel (1), and may be automatically moved from a radially retracted hooking position, in which their teeth (12) are hooked to the associated teeth (13) of the needle-covering sleeve (14), and retain it in its retracted rest position, to a radially open release position, in which their teeth (12) are disengaged from those (13) of the needle-covering sleeve (14) and release said sleeve.

3. A syringe as claimed in claim 2, characterized in that the rear end of the stem (3) of the plunger (2) is provided with means which interact with the retaining tongues (10) and automatically cause said tongues to move from their radially retracted hooking position to their radially open release position, at the end of the injection stroke of the plunger (2).

4. A syringe as claimed in claim 2, characterized in that the head (7) at the rear end of the syringe barrel (1) is hollow and open at its back, an that the retaining tongues (10) are formed by means of cuts (9) in the wall of such head (7), and have inside projections (15) protruding in the space of the hollow head (7) and interacting with a flange (8) which is located near the rear end of the stem (3) of the plunger (2), and may be housed in the hollow head (7) of the syringe barrel (1), taking therein an initial idle position, in which it does not act upon the inner projections (15) of the retaining tongues (10), the latter being in their radially retracted hooking position, and a more advanced operating position, in which it radially pushes the inner projections (15) of the retaining tongues (10) outwards and moves these tongues (10) to their radially open release position.

5. A syringe as claimed in claim 4, characterized by removable safety means (23), which lock the rear flange (8)

of the stem (3) of the plunger (2) in its initial idle position and may be manually removed so as to enable the axial forward movement of said flange (8) and hence of the stem (3) with the plunger (2).

6. A syringe as claimed in claim 5, characterized in that the removable safety means consist of a cylindrical sector (23) which may be laterally fitted outside the read head (7) of the syringe barrel (1) and removably bound thereto, and which cylindrical sector (23) has two inside clamping tongues (24), transverse to the syringe axis, and parallel to and at a certain distance from each other, which clamping tongues (24) penetrate the hollow head (7) of the syringe barrel (1) through corresponding lateral transverse slots (25) of said head (7) and are disposed one behind the other before the flange (8) of the stem (3) of the plunger (2), thereby locking it.

7. A syringe as claimed in claim 6, characterized in that the removable safety cylindrical sector (23) has hook-like means (26) which are snap-engaged with the head (7) of the syringe barrel (1) and are removably releasable therefrom.

8. A syringe as claimed in claim 1, characterized in that it has means for automatically preventing any axial backward motion the stem (3) of the plunger (2) at the end of the injection, from its corresponding advanced syringe-emptying position.

9. A syringe as claimed in claim 8, characterized in that the means for automatically preventing any axial backward motion of the stem (3) of the plunger (2) from its advanced syringe-emptying position consist of one or more reverse-lock stop projections (15) which are provided inside the rear hollow head (7) of the syringe barrel (1) on the side wall thereof and are elastically compliant radially outwards, interacting with the rear flange (8) of the stem (3) of the plunger (2) in such a way, as to enable said flange (8) to pass beyond them, at the end of the forward stroke of the plunger (2) in its advanced syringe-emptying position.

10. A syringe as claimed in claim 9, characterized in that the reverse-lock stop projections, interacting with the flange (8) of the stem (3) of the plunger (2) consist of inner projections (15) of the retaining tongues as claimed in claim 4.

11. A syringe as claimed in claim 1, characterized in that the needle-covering sleeve (14) is provided, at its rear end, in an angularly staggered position with respect to its hook-like teeth (13), with side wings (114) which may be used to grasp by two fingers the syringe barrel (1), during the injection.

12. A syringe as claimed in claim 1, characterized in that the stem (3) of the plunger (2) has a push-head (27) at its rear end.

13. A syringe as claimed in claim 1, characterized in that the sleeve-clamping ring (18) is removably fastened to the syringe barrel (1), particularly in such a way as to enable it to be slipped off it, and for example force-fitted and held by friction on the syringe barrel (1).

14. A syringe as claimed in claim 1, characterized in that the needle-carrier (4) is independent of and unbound from the sleeve-clamping ring (18).

15. A syringe as claimed in claim 1, characterized in that the sleeve-clamping ring (18) is stably and unremovably bound to the needle-carrier (4).

16. A syringe as claimed in claim 1, characterized in that the sleeve-clamping ring (18) extends forwards around the needle-carrier (4).

17. A syringe as claimed in claim 15, characterized in that the needle-carrier (4) is screwed in an inner thread (22) of the sleeve-clamping ring (18).

* * * * *